United States Patent
Trampota et al.

(10) Patent No.: US 11,504,355 B2
(45) Date of Patent: Nov. 22, 2022

(54) ERGOTHIONEINE COMPOSITIONS AND METHODS FOR MAINTAINING AND/OR INCREASING VITAMIN C LEVELS IN CELLS AND ORGANISMS

(71) Applicants: Mironova Innovations, LLC, Fairfield, NJ (US); Jan Trampota, Fairfield, NJ (US)

(72) Inventors: Jan Trampota, Fairfield, NJ (US); Daniel B. Yarosh, Merrick, NY (US)

(73) Assignee: MIRONOVA INNOVATIONS, LLC, Fairfield, NJ (US)

( * ) Notice: Subject to any disclaimer, the term of this patent is extended or adjusted under 35 U.S.C. 154(b) by 52 days.

(21) Appl. No.: 16/978,673

(22) PCT Filed: Mar. 1, 2019

(86) PCT No.: PCT/US2019/020382
§ 371 (c)(1),
(2) Date: Sep. 4, 2020

(87) PCT Pub. No.: WO2019/173159
PCT Pub. Date: Sep. 12, 2019

(65) Prior Publication Data
US 2021/0000795 A1     Jan. 7, 2021

Related U.S. Application Data (60) Provisional application No. 62/638,825, filed on Mar. 5, 2018.

(51) Int. Cl.
*A61K 31/4172* (2006.01)
*A61P 39/06* (2006.01)
*A61K 31/375* (2006.01)
*A61K 47/38* (2006.01)

(52) U.S. Cl.
CPC ........ *A61K 31/4172* (2013.01); *A61K 31/375* (2013.01); *A61K 47/38* (2013.01); *A61P 39/06* (2018.01)

(58) Field of Classification Search
CPC .............. A61K 2300/00; A61K 31/375; A61K 31/4172; A61K 47/38; A61K 8/447; A61K 8/4946; A61K 8/676; A61K 8/972; A23L 33/15; A61P 39/06; A61Q 19/08
See application file for complete search history.

(56) References Cited

U.S. PATENT DOCUMENTS

| | | |
|---|---|---|
| 2002/0110604 A1 | 8/2002 | Babish et al. |
| 2009/0142285 A1 | 6/2009 | Kurfurst et al. |
| 2012/0141611 A1 | 6/2012 | Landes et al. |

(Continued)

OTHER PUBLICATIONS

International Search Report and Written Opinion dated Jun. 5, 2019 for International Application No. PCT/US2019/020382, 17 pages.

(Continued)

*Primary Examiner* — Savitha M Rao
(74) *Attorney, Agent, or Firm* — Squire Patton Boggs (US) LLP (57) ABSTRACT

Provided herein are methods and compositions for maintaining and/or increasing vitamin C in a cell or organism. The methods and compositions are based, in part, on the synergistic effect of ergothioneine, or a derivative thereof, on vitamin C levels in cells or organisms.

21 Claims, 3 Drawing Sheets

(56) References Cited

U.S. PATENT DOCUMENTS

2016/0120781 A1   5/2016   Powell

OTHER PUBLICATIONS

Hand et al., "Biological Chemistry of Naturally Occurring Thiols of Microbial and Marine Origin", Journal of Natural Products, vol. 68, No. 2, Feb. 1, 2005, pp. 293-308.

Markova et al., "Skin cells and tissue are capable of using 1-ergothioneine as an integral component of their antioxidant defense system", Free Radical Biology and Medicine, Elsevier Inc, US, vol. 46, No. 8, Apr. 15, 2009, pp. 1168-1176.

Anonymous: "Stabilized oil-soluble vitamin C derivative VC-IP Anti-Pigmentation Age Spots Anti-oxidation DNA Protection Colorless High Skin Penetration Oil-Soluble Odorless High Safety", Mar. 31, 2014.

Mintel "UV Defense SPF 50 Ultra Facial Sunscreen" XP055591627, retrieved from www.gnpd.com Database accession No. 1855837, 7 pages.

ERGOTHIONEINE COMPOSITIONS AND METHODS FOR MAINTAINING AND/OR INCREASING VITAMIN C LEVELS IN CELLS AND ORGANISMS

CROSS-REFERENCE TO RELATED APPLICATIONS

This application is a National Stage filing under 35 U.S.C. § 371 of International Patent Application No. PCT/US2019/020382, filed Mar. 1, 2019, and entitled "ERGOTHIONEINE COMPOSITIONS AND METHODS FOR MAINTAINING AND/OR INCREASING VITAMIN C LEVELS IN CELLS AND ORGANISMS," which claims the benefit of priority to U.S. Provisional Application No. 62/638,825, filed Mar. 5, 2018, both applications of which are herein incorporated by reference in their entireties for all purposes.

FIELD

Provided herein are compositions and methods useful for maintaining or increasing vitamin C levels, and methods of their use in subjects in need thereof.

BACKGROUND OF THE INVENTION

Ergothioneine was discovered at the beginning of the 20th century in an ergot fungus contaminant of rye. Tenret, 1909, *Compt. Rend. Acad. Sci.* 149:222-224. The compound ergothioneine has been shown to protect cells from reactive oxidative species in bacteria, fungi, plants, and animals, including humans. Paul & Snyder, 2010, Cell Death Differ. 17:1134-1140; Emani et al., 2013, *Antimicrob. Agents Chemother.* 57:3202-3207. However, only certain bacteria and certain fungi have been shown to produce the compound themselves. Fahey, 2001, *Annu. Rev. Microbiol.* 55:333-356. Plants acquire ergothioneine from microbes in the soil. Audley & Tan, 1968, *Phytochemistry* 7:1999-2000. Animals, including humans, absorb ergothioneine from their diet. Humans have a specific transporter, ETT, for the uptake of ergothioneine. Gründemann et al., 22005012, *Proc. Natl. Acad. Sci. USA* 102:5256-5261. Cells that express ETT accumulate and retain ergothioneine at high levels. Id. The compound has a long biological half-life in the cell. Wolf et al., 1961, *Biochem. Biophys. Acta* 54:287-293. It is believed that ergothioneine provides antioxidant cytoprotection in such cells. Paul & Snyder, supra.

To date, ergothioneine has been proposed and used in several human and animal products. These include use as a skin toner additive (U.S. Pat. No. 7,122,211), as a photoprotective agent for human skin (U.S. Pat. No. 7,022,317), for the amelioration of liver disease (U.S. Pat. No. 6,555,141), for preventing diseases associated with oxidative damage to mitochondria (U.S. Pat. Nos. 6,479,533; 6,103,746), for repair of skin connective tissue damage (U.S. Pat. No. 6,451,771), and for other pharmaceutical antioxidant uses (U.S. Pat. Nos. 6,326,034; 6,056,965).

Vitamin C is an essential nutrient. It functions as an antioxidant and an enzyme cofactor. Vitamin C has also been suggested to be useful for therapy, for instance, in vitamin C deficiency, cardiovascular disease, cancer, and autoimmune disease. The use of vitamin C as a nutrient and for therapy has been hampered by limitations on the amount of vitamin C that can be delivered to cells.

SUMMARY OF THE INVENTION

Provided herein are methods and compositions useful, for example, for the delivery of vitamin C to cells. The methods and compositions are based, at least in part, on the striking observation that ergothioneine can boost and/or maintain levels of vitamin C in a cell. In fact, a synergistic amount of ergothioneine is shown to boost vitamin C levels in a cell by three-fold or more in the examples provided herein.

In one aspect, provided herein are methods for maintaining the amount of vitamin C in a cell. The methods comprise the step of contacting a cell that contains vitamin C with a synergistic amount of ergothioneine sufficient to maintain the level of vitamin C in the cell. In certain embodiments, the methods comprise the step of making available, to a cell that contains vitamin C, a synergistic amount of ergothioneine sufficient to maintain the level of vitamin C in the cell. Generally, the level of vitamin C is maintained in the cell with ergothioneine for a time longer than the time vitamin C would be maintained in a comparable cell in the absence of ergothioneine.

In another aspect, provided herein are methods for increasing the amount of vitamin C in a cell. The methods comprise the step of contacting a cell that contains vitamin C with a synergistic amount of ergothioneine sufficient to increase the level of vitamin C in the cell. In certain embodiments, the methods comprise the step of making available, to a cell that contains vitamin C, a synergistic amount of ergothioneine sufficient to increase the level of vitamin C in the cell. Generally, the level of vitamin C is increased in the cell with ergothioneine to an amount greater than the amount vitamin C would be maintained in a comparable cell in the absence of ergothioneine.

In another aspect, provided herein are compositions comprising vitamin C and a synergistic amount of ergothioneine. In the methods and compositions, the vitamin C can be any form recognized by those of skill in the art. In the methods and compositions, the ergothioneine can be any form of ergothioneine recognized by those of skill in the art.

In certain embodiments, the methods and compositions provided herein are useful in the prevention and treatment of conditions or diseases amenable to treatment or prophylaxis with vitamin C. These include, but are not limited to, vitamin C deficiency, oxidative stress, proliferative disease, cardiovascular disease, and autoimmune disease.

A method for the treatment or prevention of a vitamin C responsive condition or disease in a subject, including a human, is also provided that includes administering a method or composition provided herein, optionally in a pharmaceutically acceptable carrier.

In another aspect, provided herein are pharmaceutical compositions, single unit dosage forms, and kits suitable for use in treating or preventing such disorders, which comprise a therapeutically or prophylactically effective amount of a composition provided herein and one or more pharmaceutically acceptable carriers, excipients, or diluents.

DETAILED DESCRIPTION

Provided herein are methods and compositions useful for maintaining and/or increasing vitamin C levels. The methods and compositions relate to synergistic amounts of vitamin C and ergothioneine.

Definitions

When referring to the methods and compounds described herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

"Vitamin C" refers to vitamin C in any form recognized by those of skill in the art, including derivatives of vitamin C, and salts of vitamin C and derivatives. In particular embodiments, vitamin C, or a derivative thereof, is selected from the group consisting of ascorbyl palmitate, disodium isostearyl 2-0 L-ascorbyl phosphate, sodium ascorbyl phosphate, magnesium ascorbyl phosphate, tetrahexyldecyl ascorbate (BV-OSC), ascorbic acid sulfate, ascorbyl glucoside, aminopropyl ascorbyl phosphate, sodium ascorbate, L-ascorbic acid 2-sulfate dipotassium salt, and combinations thereof. Vitamin C may be obtained or produced by any method or source known to those of skill in the art, including commercial sources.

"Ergothioneine" refers to ergothioneine in any form recognized by those of skill in the art, including derivatives of ergothioneine, and salts of ergothioneine and derivatives. In particular embodiments, ergothioneine, or a derivative thereof, is selected from the group consisting of L-ergothioneine, beta-hydroxyergothioneiene, gastrolathioneine, S-methyl ergothioneine, and selenoneine. Ergothioneine may be obtained or produced by any method or source known to those of skill in the art, including commercial sources.

"Salt" refers to any salt of a compound provided herein. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

In certain embodiments, the salt of a compound provided herein retains its biological properties and is not toxic or otherwise undesirable for pharmaceutical use.

The term "substantially free of" or "substantially in the absence of" with respect to a composition refers to a composition that includes at least about 85 or 90% by weight, in certain embodiments at least about 95%, 98%, 99% or 100% by weight, of a designated enantiomer or stereoisomer of a compound. For example, "substantially free of" or "substantially in the absence of" with respect to a composition can refer to a composition that includes about 85%, 86%, 87%, 88%, 89%, 90%, 91%, 92%, 93%, 94%, 95%, 96%, 97%, 98%, 99%, or 100% by weight of a designated enantiomer or stereoisomer of a compound. In certain embodiments, in the methods and compounds provided herein, the compounds are substantially free of other enantiomers or stereoisomers.

Similarly, the term "isolated" with respect to a composition refers to a composition that includes at least 85, 90%, 95%, 98%, and 99% to 100% by weight, of a designated compound, enantiomer, or stereoisomer, the remainder comprising other chemical species, enantiomers, or stereoisomers. For example, "isolated" with respect to a composition can refer to a composition that includes about 85%, 86%, 87%, 88%, 89%, 90%, 91%, 92%, 93%, 94%, 95%, 96%, 97%, 98%, 99%, or 100% by weight of a designated compound, enantiomer, or stereoisomer, the remainder comprising other chemical species, enantiomers, or stereoisomers.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

As used herein, the terms "subject" and "patient" are used interchangeably herein. The terms "subject" and "subjects" refer to an animal, such as a mammal including a nonprimate (e.g., a cow, pig, horse, cat, dog, rat, and mouse) and a primate (e.g., a monkey such as a cynomolgus monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder (, or to enhance or improve the prophylactic effect(s) of another therapy (e.g., another prophylactic agent).

Methods

Provided herein are methods for maintaining and/or increasing vitamin C levels in a cell. The methods are based, at least in part, on the striking discovery that relatively small amounts of ergothioneine can maintain and/or increase vitamin C levels in a cell longer than are greater than, respectively, vitamin C levels in a comparable cell in the absence of vitamin C.

In the methods, a cell containing vitamin C is provided. The cell can be any cell known to those of skill in the art. In particular embodiments, the cell is a cell that has a need for vitamin C levels. The cell can be a skin cell, an epithelial cell, a neural cell, a fibroblast cell, or any other cell deemed suitable to those of skill in the art. In certain embodiments, the cell is isolated. In certain embodiments, the cell is in vitro. In certain embodiments, the cell is in vivo. In certain embodiments, the cell is part of a tissue. In certain embodiments, the cell is part of an organ. In certain embodiments, the cell is part of an organism. The cell can be contacted with the compound of interest by any technique deemed suitable by the practitioner of skill. In certain embodiments, the methods comprise the step of making the compound available to the cell.

In particular embodiments, the methods are administered to a subject. The subject can be any subject deemed suitable to the practitioner of skill. In certain embodiments, the subject is a human. In certain embodiments, the subject is in need of vitamin C. In certain embodiments, the subject has a condition or disease responsive to vitamin C.

The vitamin C can be vitamin C in any form known to those of skill in the art. In particular embodiments, the vitamin C is ascorbic acid or ascorbate, or a combination thereof. In certain embodiments, the vitamin C is a derivative of vitamin C. The derivative can be any derivative of vitamin C recognized by those of skill in the art. Particular derivatives include some chemical structure of ascorbic acid and at least some function of ascorbic acid. In particular embodiments, the vitamin C is selected from the group consisting of ascorbyl palmitate, disodium isostearyl 2-0 L-ascorbyl phosphate, sodium ascorbyl phosphate, magnesium ascorbyl phosphate, tetrahexyldecyl ascorbate (BV-OSC), ascorbic acid sulfate, ascorbyl glucoside, aminopropyl ascorbyl phosphate, sodium ascorbate, L-ascorbic acid 2-sulfate dipotassium salt, and combinations thereof. Vitamin C can be prepared or obtained by any method useful to those of skill in the art. In certain embodiments, vitamin C is obtained commercially.

The vitamin C can be in the cell by any process apparent to those of skill in the art. In certain embodiments, the vitamin C is within the cell naturally as a result of natural delivery to the cell. For instance, the vitamin C can be within the cell as a result of nutrition delivered to the cell by its host tissue, organ, or organism. In certain embodiments, the vitamin C is administered to the cell by a practitioner of skill. In certain embodiments, the vitamin C is administered by the subject hosting the cell.

In the methods, the cell is contacted with ergothioneine in an amount sufficient to maintain and/or increase the level of vitamin C in the cell. In certain embodiments, the amount of ergothioneine is sufficient to maintain the level of vitamin C in the cell for a time that is longer than the time that a comparable amount of vitamin C is maintained in a comparable cell in the absence of the ergothioneine. In certain embodiments, the level of vitamin C is maintained for a time that is about 10% to about 1000% longer. In certain embodiments, the level of vitamin C is maintained for a time that is about 10% to about 750% longer. In certain embodiments, the level of vitamin C is maintained for a time that is about 10% to about 500% longer. In certain embodiments, the level of vitamin C is maintained for a time that is about 10% to about 250% longer. In certain embodiments, the level of vitamin C is maintained for a time that is about 10% to about 200% longer. In certain embodiments, the level of vitamin C is maintained for a time that is about 10% to about 100% longer. In certain embodiments, the level of vitamin C is maintained for a time that is about 10%, about 20%, about 25%, about 50%, about 75%, about 100%, about 150%, about 200%, about 250%, about 300%, about 400%, about 500%, about 750%, or about 1000% longer.

In certain embodiments, the amount of ergothioneine is sufficient to increase the level of vitamin C in the cell to an amount that is greater than the comparable amount of vitamin C in a comparable cell in the absence of the ergothioneine. In certain embodiments, the level of vitamin C is about 10% to about 1000% greater. In certain embodiments, the level of vitamin C is about 10% to about 750% greater. In certain embodiments, the level of vitamin C is about 10% to about 500% greater. In certain embodiments, the level of vitamin C is about 10% to about 250% greater. In certain embodiments, the level of vitamin C is about 200% greater. In certain embodiments, the level of vitamin C is about 10% to about 100% greater. In certain embodiments, the level of vitamin C is about 10%, about 20%, about 25%, about 50%, about 75%, about 100%, about 150%, about 200%, about 250%, about 300%, about 400%, about 500%, about 750%, or about 1000% greater.

In certain embodiments, the level of vitamin C is both maintained and increased as described in the paragraphs above in the presence of the ergothioneine. In certain embodiments, the methods result in synergistic increase in protection against free radical damage in the cell. In certain embodiments, the methods result in result in a synergistic increase in protection against oxidative stress in the cell. As used herein, the term synergistic refers to an effect that is more than the additive combination of the effect of ergothioneine alone and the effect of vitamin C alone.

The ergothioneine can be ergothioneine in any form known to those of skill in the art. In certain embodiments, the ergothioneine is a derivative of ergothioneine. The derivative can be any derivative of ergothioneine recognized by those of skill in the art. Particular derivatives include some chemical structure of ergothioneine and at least some function of ergothioneine. In particular embodiments, the L-ergothioneine, beta-hydroxyergothioneiene, gastrolathioneine, S-methyl ergothioneine, and selenoneine, and combinations thereof Ergothioneine can be prepared or obtained by any method useful to those of skill in the art. In certain embodiments, ergothioneine is obtained commercially.

In certain embodiments, the cell is contacted with vitamin C, then the cell is contacted with ergothioneine. In certain embodiments, the cell is contacted with vitamin C and with ergothioneine simultaneously. In certain embodiments, the cell is contacted with ergothioneine, then the cell is contacted with vitamin C.

In certain embodiments, the cell is contacted with vitamin C and ergothioneine in a particular mass ratio. In certain embodiments, the practitioner of skill in the art can determine the mass ratio of vitamin C to ergothioneine that provides the desired level of vitamin C in the cell. In certain embodiments, the mass ratio of vitamin C to ergothioneine is about 50:1. In certain embodiments, the mass ratio of vitamin C to ergothioneine is about 100:1. In certain embodiments, the mass ratio of vitamin C to ergothioneine is about 150:1. In certain embodiments, the mass ratio of vitamin C to ergothioneine is about 200:1. In certain embodiments, the mass ratio of vitamin C to ergothioneine is about 250:1. In certain embodiments, the mass ratio of vitamin C to ergothioneine is about 300:1. In certain embodiments, the mass ratio of vitamin C to ergothioneine is about 400:1. In certain embodiments, the mass ratio of vitamin C to ergothioneine is about 500:1. In certain embodiments, the mass ratio of vitamin C to ergothioneine is greater than about 500:1.

In certain embodiments, the cell is contacted with vitamin C and ergothioneine in a particular molar ratio. In certain embodiments, the practitioner of skill in the art can determine the molar ratio of vitamin C to ergothioneine that provides the desired level of vitamin C in the cell. In certain embodiments, the molar ratio of vitamin C to ergothioneine is about 50:1. In certain embodiments, the molar ratio of vitamin C to ergothioneine is about 100:1. In certain embodiments, the molar ratio of vitamin C to ergothioneine is about 150:1. In certain embodiments, the molar ratio of vitamin C to ergothioneine is about 200:1. In certain embodiments, the molar ratio of vitamin C to ergothioneine is about 250:1. In certain embodiments, the molar ratio of vitamin C to ergothioneine is about 300:1. In certain embodiments, the molar ratio of vitamin C to ergothioneine is about 400:1. In certain embodiments, the molar ratio of vitamin C to ergothioneine is about 500:1. In certain embodiments, the molar ratio of vitamin C to ergothioneine is greater than about 500:1.

In particular embodiments, the methods are applied to a subject in need of vitamin C. In certain embodiments, ergothioneine is administered to a subject in need of vitamin C. In certain embodiments, vitamin C and ergothioneine are administered to the subject. In certain embodiments, vitamin C is administered to the subject, then ergothioneine is administered to the subject. In certain embodiments, ergothioneine is administered to the subject, then vitamin C is administered to the subject. In certain embodiments, vitamin C and ergothioneine are administered to the subject simultaneously. In certain embodiments, vitamin C and ergothioneine are administered alternately to the subject. In certain embodiments, vitamin C and ergothioneine are administered in cycling therapy to the subject.

The subject can be any subject in need of vitamin C. In certain embodiments, the subject is a human. In certain embodiments, the subject is a human in need of vitamin C therapy. The administration can be by any route of administration deemed suitable by the practitioner of skill. In certain embodiments, the vitamin C and ergothioneine are administered by parenteral, topical, transmucosal, pulmonary, or transdermal administration.

The methods can be administered to treat or prevent any disease or condition in the subject that is responsive to vitamin C. In certain embodiments, the methods are administered to treat or prevent vitamin C deficiency. In certain embodiments, the methods are administered to treat or prevent oxidative stress. In certain embodiments, the methods are administered to treat or prevent a proliferative disease. In certain embodiments, the methods are administered to treat or prevent cancer. In certain embodiments, the methods are administered to treat or prevent cardiovascular disease. In certain embodiments, the methods are administered to treat or prevent atherosclerosis. In certain embodiments, the methods are administered to treat or prevent autoimmune disease. In certain embodiments, the methods are administered to treat or prevent rheumatoid arthritis. In certain embodiments, the methods are administered to treat or prevent age-related macular degeneration.

The vitamin C and ergothioneine can be administered individually or together by standard techniques. In certain embodiments, vitamin C is administered in a pharmaceutical composition. In certain embodiments, ergothioneine is administered in a pharmaceutical composition. In certain embodiments, vitamin C and ergothioneine are administered in together in a pharmaceutical composition.

Compositions

In certain embodiments, provided herein are compositions comprising vitamin C and ergothioneine. The vitamin C can be any vitamin C described herein. The ergothioneine can be any ergothioneine described herein.

In particular embodiments, the ergothioneine is present in a synergistic amount with vitamin C. In certain embodiments, the ergothioneine is present in an amount sufficient to maintain the level of vitamin C in a target cell, tissue, organ, or organism for a time that is longer than the time that a comparable amount of vitamin C is maintained in a comparable cell, tissue, organ, or organism in the absence of the ergothioneine. In certain embodiments, the ergothioneine is present in an amount sufficient to increase the level of vitamin C in a target cell, tissue, organ, or organism to a level that is greater than the level of vitamin C is in a comparable cell, tissue, organ, or organism in the absence of the ergothioneine.

In certain embodiments, the vitamin C and ergothioneine are in a particular mass ratio. In certain embodiments, the practitioner of skill in the art can determine the mass ratio of vitamin C to ergothioneine that provides the desired level of vitamin C. In certain embodiments, the mass ratio of vitamin C to ergothioneine is about 50:1. In certain embodiments, the mass ratio of vitamin C to ergothioneine is about 100:1. In certain embodiments, the mass ratio of vitamin C to ergothioneine is about 150:1. In certain embodiments, the mass ratio of vitamin C to ergothioneine is about 200:1. In certain embodiments, the mass ratio of vitamin C to ergothioneine is about 250:1. In certain embodiments, the mass ratio of vitamin C to ergothioneine is about 300:1. In certain embodiments, the mass ratio of vitamin C to ergothioneine is about 400:1. In certain embodiments, the mass ratio of vitamin C to ergothioneine is about 500:1. In certain embodiments, the mass ratio of vitamin C to ergothioneine is greater than about 500:1.

In certain embodiments, the vitamin C and ergothioneine are in a particular molar ratio. In certain embodiments, the practitioner of skill in the art can determine the molar ratio of vitamin C to ergothioneine that provides the desired level of vitamin C. In certain embodiments, the molar ratio of vitamin C to ergothioneine is about 50:1. In certain embodiments, the molar ratio of vitamin C to ergothioneine is about 100:1. In certain embodiments, the molar ratio of vitamin C to ergothioneine is about 150:1. In certain embodiments, the molar ratio of vitamin C to ergothioneine is about 200:1. In certain embodiments, the molar ratio of vitamin C to ergothioneine is about 250:1. In certain embodiments, the molar ratio of vitamin C to ergothioneine is about 300:1. In certain embodiments, the molar ratio of vitamin C to ergothioneine is about 400:1. In certain embodiments, the molar ratio of vitamin C to ergothioneine is about 500:1. In certain embodiments, the molar ratio of vitamin C to ergothioneine is greater than about 500:1.

In particular embodiments, the composition further comprises one or more pharmaceutically acceptable carriers. Exemplary pharmaceutically acceptable carriers are described below. In particular embodiments, the composition further comprises microcrystalline cellulose. In certain embodiments, the ergothioneine is dispersed on microcrystalline cellulose.

Pharmaceutical and Nutraceutical Compositions and Routes of Administration

The compositions provided herein can be formulated as pharmaceutical compositions using methods available in the art and those disclosed herein. Any of the compositions disclosed herein can be provided in the appropriate pharmaceutical composition and be administered by a suitable route of administration. The compositions provided herein can also be formulated as nutraceutical or nutritional formulations with additives such as nutraceutically or nutritionally acceptable excipients, nutraceutically or nutritionally acceptable carriers, and nutraceutically or nutritionally acceptable vehicles.

The methods provided herein encompass administering pharmaceutical or nutraceutical compositions containing at least one compound as described herein, either used alone or in the form of a combination with one or more compatible and pharmaceutically acceptable carriers, such as diluents or adjuvants. In certain embodiments, ergothioneine and vitamin C are formulated together. In certain embodiments, ergothioneine and vitamin C are packaged together.

In clinical practice the compositions provided herein may be administered by any conventional route, in particular orally, parenterally, rectally or by inhalation (e.g. in the form of aerosols). In certain embodiments, the compositions provided herein are administered orally.

The compositions can be prepared as nutritional formulations such as foods, including medical or functional foods and dietary supplements. A "medical or functional food" is defined as being consumed as part of a usual diet which has been demonstrated to have physiological benefits and/or to reduce the risk of chronic disease beyond basic nutritional functions. A "dietary supplement" is defined as a product that is intended to supplement the human diet and is typically provided in the form of a pill, capsule, tablet, or like formulation. By way of example, but not limitation, a dietary supplement may include one or more of the following ingredients: vitamins, minerals, herbs, botanicals, amino acids, dietary substances intended to supplement the diet by increasing total dietary intake, and concentrates, metabolites, constituents, extracts or combinations of any of the foregoing. Dietary supplements may also be incorporated into food stuffs, such as functional foods designed to promote health or to prevent disease or disorders. If administered as a medicinal preparation, the composition can be administered, either as a prophylaxis or treatment, to a patient in any of a number of methods. The subject compositions may be administered alone or in combination with other pharmaceutical agents and can be combined with a physiologically acceptable carrier thereof. The effective amount and method of administration of the particular formulation can vary based on the individual subject, the stage of disease, and other factors evident to one skilled in the art. During the course of the treatment, the concentration of the subject compositions may be monitored (for example, blood plasma levels may be monitored) to insure that the desired level is maintained.

The term "nutraceutical" has been used to refer to any substance that is a food or a part of a food and provides medical or health benefits, including the prevention and treatment of disease. Hence, compositions falling under the label "nutraceutical" may range from isolated nutrients, dietary supplements and specific diets to genetically engineered designer foods, herbal products, and processed foods such as cereals, soups and beverages. In a more technical sense, the term has been used to refer to a product isolated or purified from foods, and generally sold in medicinal forms not usually associated with food and demonstrated to have a physiological benefit or provide protection against chronic disease.

In pharmaceutical compositions, use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmacopeia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound(s).

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail in the sections above. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th, 18th and 20th eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, $16^{th}$, 18th and $20^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses for each compound are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of each active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described provide each compound within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of each compound of a composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of each compound provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance dose is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail above. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

In certain embodiments, each active agent, vitamin C and ergothioneine, is administered separately. In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, the compounds are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compounds provided herein are cyclically administered to a patient. Cycling therapy involves the administration of a first agent for a period of time, followed by the administration of a second agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the compounds provided herein are administered in a cycle of less than about 3 weeks, about once every two weeks, about once every 10 days or about once every week. One cycle can comprise the administration of a compounds provided herein by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of each agent are administered separately yet within a time interval such that the compounds provided herein can work together. For example, one component can be administered once per week in combination with the other components that can be administered once every two weeks or once every three weeks. In other words, the dosing regimens are carried out concurrently even if the therapeutics are not administered simultaneously or during the same day.

Kits

Also provided are kits for use in methods. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Assay Methods

Compounds can be assayed for amounts or activity according to any assay known to those of skill in the art.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); mM (millimolar); µM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Vitamin C Assays

This example provides methods and results from studies evaluating the effect of ergothioneine on vitamin C in human fibroblast cells.

Human skin fibroblasts were cultured for 18 hours in T-25 flasks. Cells were incubated with 1) control solution, 2) magnesium ascorbyl phosphate, or 3) magnesium ascorbyl phosphate+ergothioneine (1:100). Cells in each group were then treated for 6 hours with a) control solution or b) 500 µM alloxan to induce oxidative stress. All samples were assayed for ascorbic acid with an ascorbic acid colorimetric assay (Biovision catalog no. K671).

Results are provided in the table below, where ascorbic acid content (nmol) in human skin fibroblasts per one million cells is reported.

| Test solutions and compounds | Sample A | Sample B | Ave | STDEV |
|---|---|---|---|---|
| 5% of EGT + MAP solution | 51.17 | 49.63 | 50.40 | 1.09 |
| 1.58% of EGT + MAP solution | 51.29 | 48.31 | 49.80 | 2.11 |
| 0.5% of EGT + MAP solution | 18.59 | 19.79 | 19.19 | 0.85 |
| 0.158% of EGT + MAP solution | 11.71 | 11.25 | 11.48 | 0.32 |
| 0% of EGT + MAP solution | 3.06 | 2.89 | 2.98 | 0.12 |
| 5% of MAP solution | 50.20 | 51.35 | 50.77 | 0.81 |
| 1.58% of MAP solution | 49.23 | 50.54 | 49.89 | 0.93 |
| 0.5% of MAP solution | 21.68 | 21.33 | 21.51 | 0.24 |
| 0.158% of MAP solution | 9.94 | 10.34 | 10.14 | 0.28 |
| 0% of MAP solution | 2.89 | 2.84 | 2.86 | 0.04 |
| 5% of EGT + MAP solution with 500 uM Alloxan | 42.41 | 42.58 | 42.50 | 0.12 |
| 1.58% of EGT + MAP solution with 500 uM Alloxan | 28.38 | 28.38 | 28.38 | 0.00 |
| 0.5% of EGT + MAP solution with 500 uM Alloxan | 11.94 | 11.77 | 11.86 | 0.12 |
| 0.158% of EGT + MAP solution with 500 uM Alloxan | 6.21 | 6.21 | 6.21 | 0.00 |
| 0% of EGT + MAP with 500 uM Alloxan | 2.89 | 2.89 | 2.89 | 0.00 |
| 5% of MAP solution with 500 uM Alloxan | 13.37 | 13.37 | 13.37 | 0.00 |
| 1.58% of MAP solution with 500 uM Alloxan | 11.88 | 12.46 | 12.17 | 0.40 |
| 0.5% of MAP solution with 500 uM Alloxan | 9.54 | 9.99 | 9.77 | 0.32 |
| 0.158% of MAP solution with 500 uM Alloxan | 4.84 | 5.01 | 4.93 | 0.12 |
| 0% of MAP solution with 500 uM Alloxan | 2.55 | 2.66 | 2.61 | 0.08 |

Figure 1:
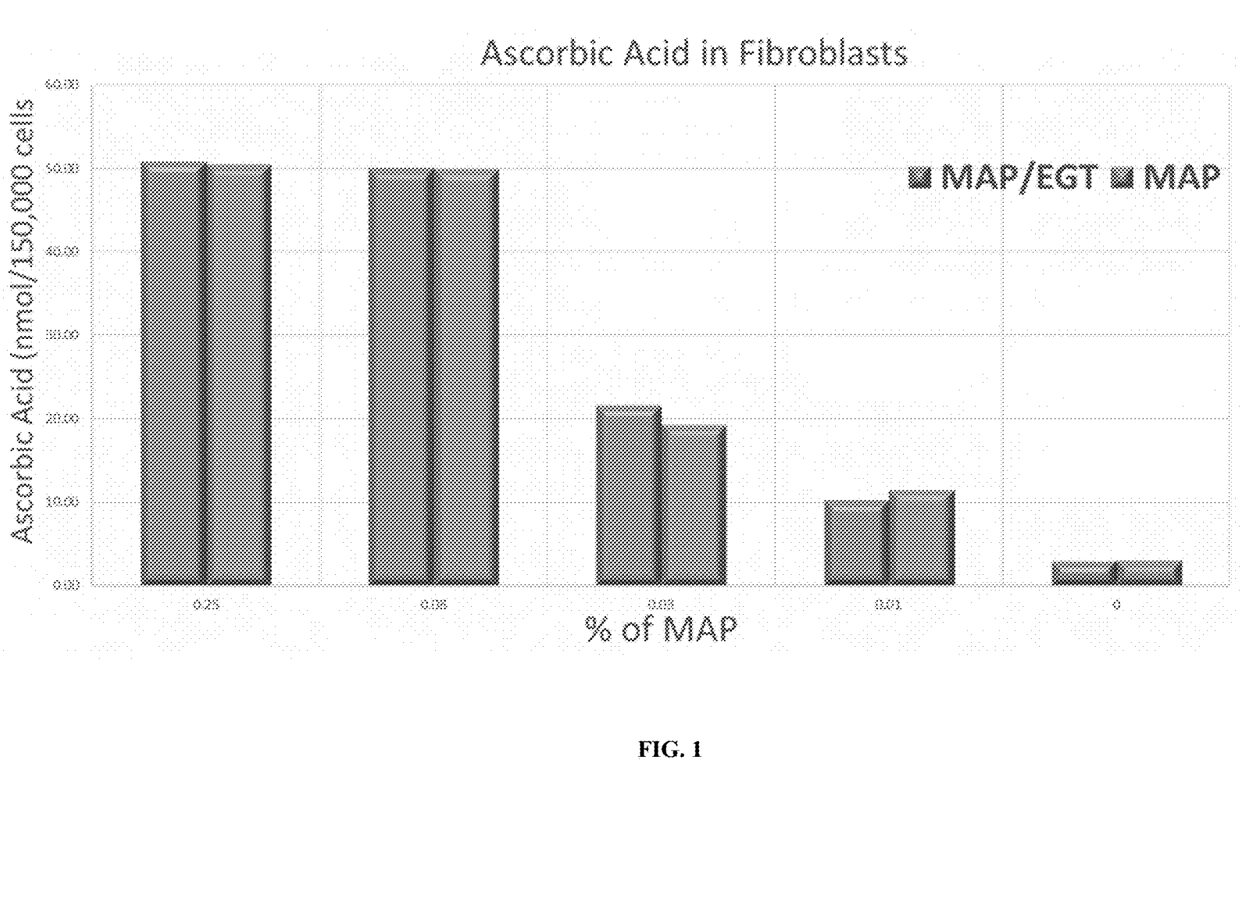
FIG. 1 provides vitamin C absorbed by fibroblast cells in the presence and absence of ergothioneine, or EGT. Vitamin C is in the form of magnesium ascorbyl phosphate, or MAP.
Figure 2:
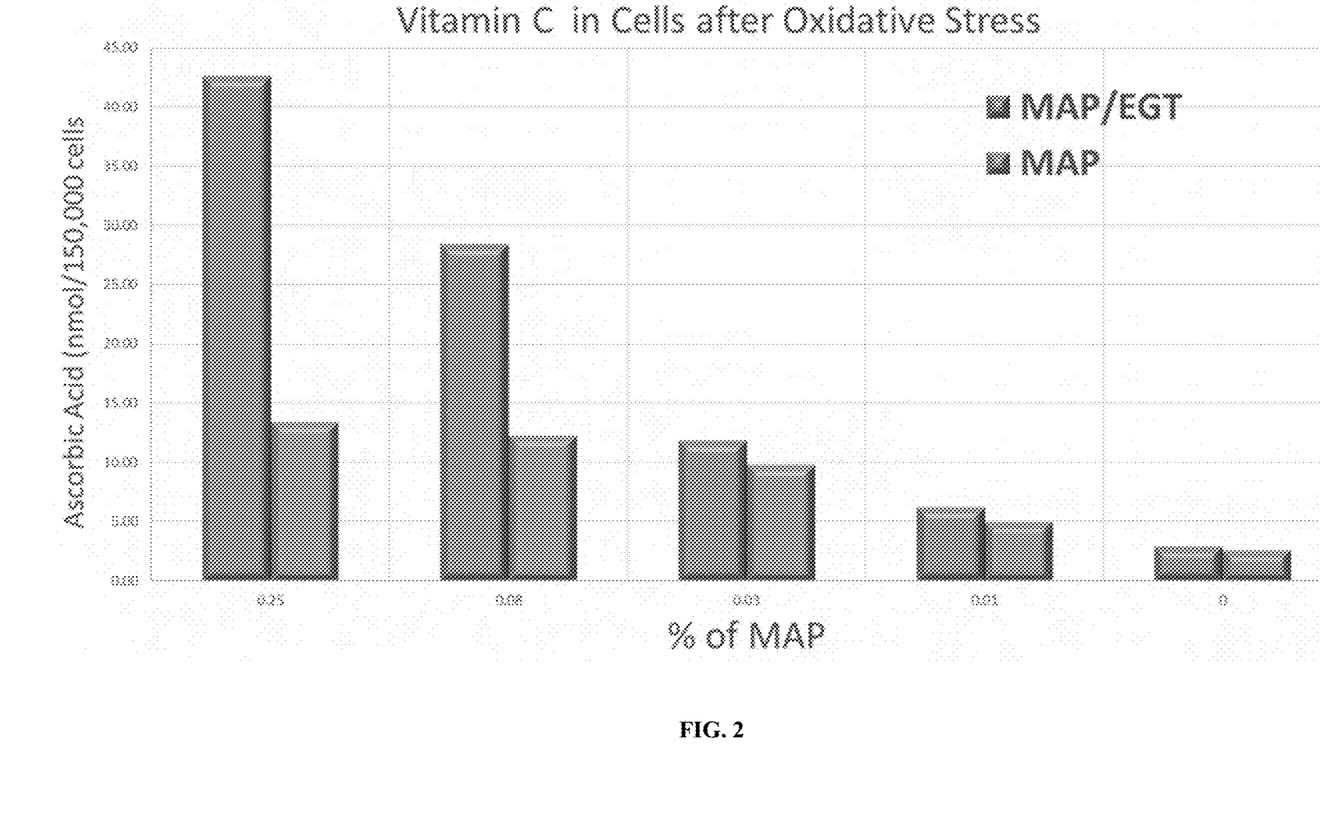
FIG. 2 provides vitamin C levels in fibroblast cells following oxidative stress, in the presence or absence of ergothioneine, EGT. Vitamin C is in the form of magnesium ascorbyl phosphate, or MAP.
Figure 3:
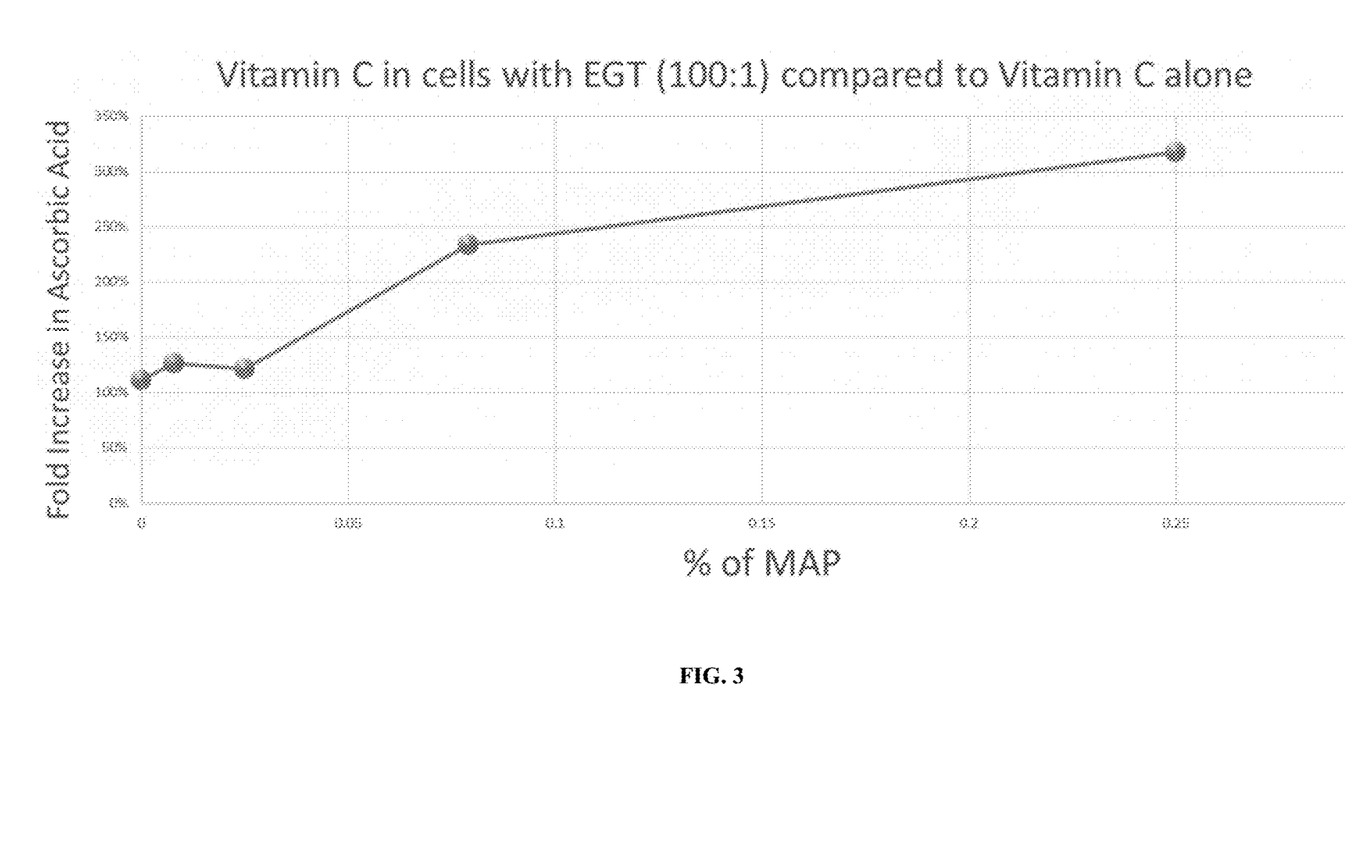
FIG. 3 provides the increase in amount of vitamin C in cells as a function of ergothioneine, or EGT. Vitamin C is in the form of magnesium ascorbyl phosphate, or MAP.

As shown in FIG. 1, ascorbic acid was equally absorbed by the fibroblast cells when treated with or without ergothioneine. Following oxidative stress, as shown in FIG. 2, ascorbic acid was substantially greater in cells treated with ergothioneine and magnesium ascorbyl phosphate (MAP/EGT) compared to cells treated with magnesium ascorbyl phosphate alone (MAP). As shown in FIG. 3, the amount of ascorbic acid in fibroblast cells following oxidative stress was synergistically increased in the presence of ergothioneine. Administering just 1:100 ergothioneine (EGT) to magnesium ascorbyl phosphate (MAP) increased ascorbic acid levels up to 300% following oxidative stress.

All publications and patent, applications cited in this specification are herein incorporated by reference as if each individual publication or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the subject matter limited solely by the scope of the following claims, including equivalents thereof.

What is claimed:

1. A method for maintaining and/or increasing the ascorbic acid level in a cell, the method comprising the steps of:
  a. contacting the cell with ergothioneine, or a derivative thereof; and
  b. contacting the cell with a vitamin C composition before, after, or simultaneous with contacting the cell with ergothioneine, or a derivative thereof,
  wherein the vitamin C composition comprises ascorbic acid or ascorbate,
  wherein the ascorbic acid or ascorbate is in a mass amount relative to the ergothioneine ranging from 50:1 to greater than 500:1, thereby maintaining and/or increasing the level of ascorbic acid in the cell, and
  wherein the ergothioneine derivative is selected from the group consisting of L-ergothioneine, beta-hydroxyergothioneine, gastrolathioneine, S-methyl ergothioneine, and selenoneine.

2. The method of claim 1, wherein the ascorbic acid level is maintained.

3. The method of claim 1, wherein the ascorbic acid level is increased.

4. The method of claim 1, wherein the ascorbic acid level is maintained and increased compared to the level of ascorbic acid in the absence of the ergothioneine, or derivative thereof.

5. The method of claim 1, wherein the amount of ergothioneine, or derivative thereof, is sufficient to maintain the level of ascorbic acid in the cell at least 10%, 20%, 25%, 50%, 75%, 100%, 150%, 200%, 250%, 300%, or more, longer than the level of ascorbic acid would be maintained in the cell in the absence of the ergothioneine, or derivative thereof.

6. The method of claim 1, wherein the amount of ergothioneine, or derivative thereof, is sufficient to increase the level of ascorbic acid in the cell to a level that is at least 10%, 20%, 25%, 50%, 75%, 100%, 150%, 200%, 250%, 300%, or more, greater than the level of ascorbic acid that would be in the cell in the absence of the ergothioneine, or derivative thereof.

7. The method of claim 1, wherein the mass ratio of ascorbic acid or ascorbate, to ergothioneine, or derivative thereof, is 50:1, 100:1, 150:1, 200:1, 250:1, 300:1, 400:1, or 500:1.

8. The method of claim 1, wherein the molar ratio of ascorbic acid or ascorbate, to ergothioneine, or derivative thereof, is 50:1, 100:1, 150:1, 200:1, 250:1, 300:1, 400:1, or 500:1.

9. The method of claim 1, wherein the vitamin C composition and ergothioneine, or derivative thereof, are administered to a subject.

10. The method of claim 1, wherein the vitamin C composition and ergothioneine, or derivative thereof, are administered by parenteral, topical, transmucosal, pulmonary, or transdermal administration.

11. A method of synergistically increasing protection against free radical damage in a cell, comprising the method of claim 1.

12. A method of synergistically increasing protection against oxidative stress in a cell, comprising the method of claim 1.

13. A method of treating a vitamin C responsive condition in a subject in need thereof, comprising administering the step(s) of claim 1 to the subject in need of vitamin C treatment.

14. The method of claim 13, wherein the condition is selected from the group consisting of vitamin C deficiency, oxidative stress, cancer, cardiovascular disease, atherosclerosis, rheumatoid arthritis, and age-related macular degeneration.

15. The method of claim 13, wherein the ergothioneine is administered in a pharmaceutical composition further comprising one or more pharmaceutically acceptable carriers.

16. A pharmaceutical or nutraceutical composition comprising a vitamin C composition and ergothioneine, or derivative thereof,
   wherein the vitamin C composition comprises ascorbic acid or ascorbate,
   wherein the ascorbic acid or ascorbate is in a mass amount relative to the ergothioneine ranging from 50:1 to greater than 500:1, and
   wherein the ergothioneine derivative is selected from the group consisting of L-ergothioneine, beta-hydroxyergothioneine, gastrolathioneine, S-methyl ergothioneine, and selenoneine.

17. The pharmaceutical or nutraceutical composition of claim 16, wherein the mass ratio of ascorbic acid or ascorbate to ergothioneine, or derivative thereof, is 50:1, 100:1, 150:1, 200:1, 250:1, 300:1, 400:1, or 500:1.

18. The pharmaceutical or nutraceutical composition of claim 16, wherein the molar ratio of ascorbic acid or ascorbate to ergothioneine, or derivative thereof, is 50:1, 100:1, 150:1, 200:1, 250:1, 300:1, 400:1, or 500:1.

19. The pharmaceutical or nutraceutical composition of claim 16, further comprising one or more pharmaceutically acceptable carriers.

20. The pharmaceutical or nutraceutical composition of claim 19, further comprising microcrystalline cellulose.

21. The pharmaceutical or nutraceutical composition of claim 20, wherein the ergothioneine, or derivative thereof, is dispersed on microcrystalline cellulose.

* * * * *